United States Patent [19]
Dziondziak

[11] Patent Number: 4,814,188
[45] Date of Patent: Mar. 21, 1989

[54] METHOD FOR THE PRODUCTION OF LOW-ALCOHOL OR ALCOHOL-FREE BEER

[75] Inventor: Klaus Dziondziak, Pinneberg, Fed. Rep. of Germany

[73] Assignee: Holsten-Brauerei AG, Hamburg, Fed. Rep. of Germany

[21] Appl. No.: 47,466

[22] Filed: May 11, 1987

[30] Foreign Application Priority Data

May 13, 1986 [DE] Fed. Rep. of Germany ....... 3616094

[51] Int. Cl.$^4$ ............................................. C12C 11/00
[52] U.S. Cl. ........................................... 426/7; 426/16; 426/29; 426/62; 426/477; 426/592
[58] Field of Search ................... 426/7, 14, 16, 28, 62, 426/29, 474–477, 592, 487, 490, 488

[56] References Cited

PUBLICATIONS

M. Ciriacy: "Genetics of Alcohol Dehydrogenase in Saccharomyces Cerevisiae", I. Isolation and Genetic Analysis of adh Mutants, Mutation Research 29 (1975), pp. 315–326.
Williamson et al, "Use of Transformation and Meiotic Gene Conversion to Construct a Yeast Strain COntaining a Deletion in the Alcohol Dehydrogenase I Gene", in: Genetic Engineering in Eukaryotes, Lurquin, P. F. and Kleinhofs, A. (ed.) Plenum Publishing Corp., N.Y., pp. 21–32 (1985).
Brauwelt 128, Nr. 15, 10. Apr. (1986), pp. 572–574.
Chemical Abstracts, Band 83, Nr. 21, 24. Nov. 1975, Seite 283, Zusammenfassung Nr. 175340b, Columbus Ohio, US: M. Ciriacy: "Genetics of Alcohol Dehydrogenase in Saccharomyces cerevisiae. I Isolation & genetic Analysis of adh mutants", & Mutat. Res. 1975, 29(3), 315–325.
Chemical Abstracts, Band 88, Nr. 21, 22. Mai 1978, Seite 298, Zusammenfassung Nr. 148877d, Columbus, Ohio US; M. Ciriacy: "A yeast mutant with glucose-resistant formation of mitochondrial enzymes", & Mol. Gen. Genet. 1978, 159(3), 329–335.
Chemical Abstracts, Band 92, Nr. 15, 14. Apr. 1980, Seite 582, Zusammenfassung Nr. 126816z, Columbus, Ohio, US; J. Dalgaard Mikkelsen et al: "Thiaisoleucine resistant mutants in Saccharomyces carlsbergensis increase the content of D–amyl alcohol in beer", & Carlsberg Res. Commun. 1979, 44(4), 219–223.

*Primary Examiner*—Marianne Cintins
*Attorney, Agent, or Firm*—Birch, Stewart, Kolasch & Birch

[57] ABSTRACT

The subject matter of the invention is a method for the production of low-alcohol or alcohol-free beer having a glycerol content of from 0.3 to 2.0% by volume, which content improves the body of the beer. In the method according to the invention, the process of fermentation is carried out using an ADH-negative yeast mutant which cannot produce alcohol, but produces increased amounts of glycerol instead. The obtained alcohol-free beer can be blended with normal, alcoholic beer to give low-alcohol beer.

9 Claims, No Drawings

METHOD FOR THE PRODUCTION OF LOW-ALCOHOL OR ALCOHOL-FREE BEER

FIELD OF THE INVENTION

The invention relates to a method for the production of low-alcohol or alcohol-free beer.

BACKGROUND OF THE INVENTION

There are already several methods known for the production of low-alcohol or alcohol-free beer. For this purpose, at least a portion of alcohol is removed from beer produced according to conventional brewing processes and having a normal alcohol content. In the method disclosed in the No. DE-A-14 42 238, alcohol is evaporated in a thin layer-evaporator at a temperature below 70 C. In the similar method known from the No. DE-A-12 66 266, beer is firstly subjected to atomisation evaporation in a vacuum and then to thin layer evaporation in a vacuum. The residuals are reblended and impregnated with carbonic acid (carbon dioxide).

Furthermore, the No. DE-A-24 05 543 and the No. DE-A-721 249 describe methods for the adsorptive alcohol removal from beer. A method for the production of low-alcohol beer by reverse osmosis is disclosed in the No. DE-A-23 23 094.

Finally, methods have been proposed in which the alcohol is distilled off in a brewing pan.

On the other hand, methods for the production of low-alcohol or alcohol-free beer have been developed in which the production of alcohol during the production process is reduced from the very beginning.

This is achieved either by using yeast that can only partially ferment wort or by repressing or interrupting fermentation; cf. No. DE-A-520 363 and No. DE-A-728 871.

All the above methods have the disadvantage in that the taste of the low-alcohol or alcohol-free beer obtained thereby is not as good as that of normal alcoholic beer. Beer which is dealcoholised after production is dull and inharmonious in taste, whereas beer in which the production of alcohol is prevented or reduced from the very beginning has the typical, unpleasant taste of wort. It has also been found that the dealcoholisation methods used entail rather high expenditure and are troublesome.

The European patent application No. 183 858, published on 11th June 1986, describes beer, in particular low-alcohol or alcohol-free beer, which is characterised in that it contains 0.3 to 2.0% by volume of glycerol which improves the body of the beer. The method described therein comprises carrying out fermentation via yeast which produces elevated amounts of glycerol and sugar alcohols, the production of ethanol being reduced at the same time.

No fermenting processes in which the production of glycerol is high and that of ethanol extremely low are known.

SUMMARY OF THE INVENTION

The object of the invention is to provide a modified method for the production of low-alcohol or alcohol-free beer having a glycerol content of 0.3 to 2.0% by volume, which content improves the body of the beer. This object is achieved by using yeast in the process of fermentation which, as a consequence of genetic modification, is not able to produce ethanol, but is able to produce increased amounts of glycerol instead. ADH-negative, in particular ADH 1-negative yeast mutants are suitable for this purpose.

Thus the subject matter of the invention is a method for the production of low-alcohol or alcohol-free bear having a glycerol content of 0.3 to 2.0% by volume, which content improves the body of the beer, which is characterised in that fermentation is carried out using an ADH-negative yeast mutant which cannot produce alcohol, but produces increased amounts of glycerol instead, and that the obtained alcohol-free beer is optionally blended with normal, alcoholic beer.

The alcohol dehydrogenase-free (ADH-free) yeast mutant used in the method of the invention is preferably an ADH negative, ADH 1-non-revertible mutant of the yeast *Saccharomyces cerevisiae*.

DETAILED DESCRIPTION OF THE INVENTION

In accordance with the relevant literature, "low-alcohol" beer is such having an ethanol content of 0.5 to 1.5% by weight. "Alcohol-free" beer is such having an ethanol content of under 0.5, preferably under 0.1, most preferably under 0.05% by weight (detection limit).

In the anaerobic metabolism of the genetically modified yeast mutants used according to the method of the invention, an increased amount of acetaldehyde is produced during fermentation.

Acetaldehyde is a cell poison and is only tolerated by yeast to a certain extent. When large amounts of acetaldehyde accumulate in the cells or in the fermenting substrate, there is a danger that the metabolic activities of the yeast will be impaired.

On the other hand, even in the finished product (normal beer) only a very small amount of acetaldehyde can be tolerated, the taste threshold value being approx. 25 ppm.

Thus the acetaldehyde, which is a metabolic product, must be removed from the beer obtained according to the method of the invention. This can be done, for example, by removing it from the finished product once the process of fermentation has been completed. In the method according to the invention, however, the acetaldehyde is preferably already removed during fermentation, especially as it has a harmful effect on the yeast cells.

In the method according to the invention, fermentation is therefore preferably carried out at a temperature higher than the boiling point of acetaldehyde, i.e. at a temperature of over 21° C. Furthermore, the fermenting substrate can be either continuously or periodically gassed in such a way that the acetaldehyde is effectively removed by the gas flowthrough. If the gassing process is accordingly intense, the acetaldehyde can be effectively removed if gassing takes place once a day for about 15 to 30 minutes.

In principle, gassing can be carried out using gases which do not impair the process of fermentation or the finished product. One can use either air or inert gases, in particular $CO_2$, under strictly anaerobic conditions. The reactor used here can have a closed system in which the gas is freed from the substances contained therein in an appropriate, known manner, so that said gas can be re-introduced into the gassing process, (e.g. via cold drying).

For the rest, the modified fermentation process is carried out in such a way that the amount of glycerol produced is optimal for harmonising the taste of the beer. The preferred content is from 0.4 to 1.5% by volume, more preferably from 0.5 to 1.2% by volume. Excess glycerol can be neutralised by decreasing the attenuation limit, whereas lack of glycerol can be compensated for by defining residual amounts of fermentable substances of the wort.

The following is a description of the production of alcohol dehydrogenase-free (ADH-free) ADH 1-non-revertible mutants of the yeast *Saccharomyces cerevisiae*. (The terminology used in (4) is valid for the designation of the ADH-genes and the ADH-isoenzymes):

1. The selection of an ADHI-negative mutant (adh1) as a 1 mM allyl alcohol-resistant mutant on a glucose-containing medium as described in (1). Genotype of the obtained isolate: adh1 ADH2 ADH3.

2. On the basis of the isolate according to 1., selection of an ADHII-negative (adh2) mutant as a 1 mM allyl alcohol-resistant mutant on a glucose-free medium as described in (1).

3. On the basis of the isolate according to 2., selection of an ADHIII-negative (adh3) mutant as a 10 mM allyl alcohol-resistant mutant on a glucose-free medium as desribed in (1). Genotype of the obtained isolate: adh1 adh2 adh3.

4. The crossing of an isolate according to 3. of the haploid strain having the genotype ADH1 ADH2 ADH3 ura3-52 (e.g. strain Y27, permanently available from the collection of the Yeast Genetic Stock Center, Berkely, U.S.A.); the sporulation of the obtained diploid cells; tetrad analysis of the obtained asci; the examination of the ADH-isoenzyme pattern in cultures derived from individual ascospores, as described in (1). The identification of isolates of the genotype ADH1 adh2 adh3 ura3-52, pairing type MAT a or MAT alpha, as described in (1).

5. The construction of an ADH1-deletion (adh1-Δ) by means of in vitro mutagenesis, as described for example in (2).

6. The transformation of the haploid yeast strain ADH1 adh2 adh3 ura3-52 with the vector obtained according to 5. and the identification of the transformants as given in (2).

7. The isolation of an ADHI-negatint mutant on the basis of one of the transformants according to 6. as described in (2). Genotype of the obtained isolate: adh1-Δ.YIp5(URA)adh1-Δ adh2 adh3 ura3-52.

8. The isolation of a vector-free (YIp5-free), ADHI-negative mutant by crossing the isolate obtained according to 7. with a haploid yeast strain obtained according to 4. having the genotype ADH1 adh2 adh3 ura3-52; the sporulation of the obtained diploid cells; the selection of 2 mM allylalcoholresistant mutants from the sporulation culture on a glucosecontaining medium as described in (1); the examination of the need for uracil; the isolation of ADHI-negative segregants which require uracil; showing the presence of the adh1-fragment and the absence of the vector sequence YIp5 used in 5. by means of the Southern method (e.g. as given in (3)). Genotype of the obtained isolates: adh1-Δ adh2 adh3 ura3-52.

9. In order to avoid the formation of increasing amounts of revertants during fermentation, it is desirable to inactivate the ADH 4 gene which is present in yeast of the genus Saccharomyces and increasingly expressed when the ADH1, the ADH2 and/or the ADH3 genes are inactivated; see Paquin and Williamson, Mol. Cell. Biol. 6, pp. 70 to 79 (1986).

Furthermore, it is also possible to produce a mutant having a non-revertibly inactivated ADH gene by deleting said gene according to the method described above.

Literature:

(1) Ciriacy, M.: Genetics of Alcohol Dehydrogenase in *Saccharomyces cerevisiae*. I. Isolation and Genetic Analysis of adh Mutants, *Mutation Research* 29: 315–326 (1975).

(2) Williamson, V. M. Beier, D. and Young, E. T.: Use of Transformation and Meiotic Gene Conversion to Construct a Yeast Strain Containing a Deletion in the Alcohol Dehydrogenase I Gene, In; Genetic Engineering in Eukaryotes, Lurquin, P. F. and Kleinhofs, A. (ed.), Plenum Publishing Corp., New York, pp. 21 to 32 (1983).

(3) Williamson, V. M., Yount, E. T., Ciriacy, M: Transposable Elements Associated with Constitutive Expression of Yeast Alcohol Dehydrogenase II Cell 23: 605–614 (1981).

(4) Tauchi, A. K. W., Ciriacy, M. and Young, E. T.: Carbon Source Dependence of Transposable Element-Associated Gene Activation in *Saccharomyces Cerevisiae*, Molec. Cell, Biology 4: 61–68 (1984).

The following example is a detailed description of a preferred embodiment of the method according to the invention:

EXAMPLE:

An ADH negative, ADH 1-non-revertible mutant of a yeast obtained according to the above described selection process is placed along with original wort into a fermenting tank having a closed $CO_2$ washing system at a temperature of 25° C. The initial cell concentration is $40 \times 10^6$ cells/ml. The content of original extract of the original wort is about 11%, the actual attenuation limit is about 67%.

The beer is almost completely fermented. The fermenting tank is washed every 24 hours for about 30 minutes with $CO_2$ in order to remove the acetic aldehyde. This is done in a cyclic manner (about 30 $m^3$/hl/h).

After final fermentation, beer having the following values is obtained:

The percentages given are percent by weight.

| | |
|---|---|
| Original wort (%) | 11 |
| Real extract (%) | 3.7 |
| Glycerol content (%) | about 1.5 |
| Ethanol (%) | 0.0 |

Once it has undergone normal maturation and storing, the bear sensorically corresponds to normal beer which was produced using the same percentage of initial wort and normal yeast. During the production of low-alcohol beer, random amounts of said beer can be blended with normal, alcoholic beer.

I claim:

1. A method for producing low-alcohol or alcohol-free beer having a glycerol content of 0.3 to 2.0% by volume which comprises:
   carrying out fermentation of said beer with a fermentation effective amount of a nonalcohol producing, glycerol producing ADH-negative yeast.

2. The method according to claim 1, wherein said ADH-negative yeast is Saccharomyces cervisiae.

3. The method according to claim 1, wherein said ADH negative yeast is an ADH 1-non-revertible yeast mutant.

4. The method according to claim 1, wherein said ADH negative yeast is selected from the group consisting of ADH 1- and ADH 4-non-revertible yeast mutants.

5. The method according to claim 1, wherein said ADH negative yeast is selected from the group consisting of ADH 1-, ADH 3- and ADH 4-non-revertible yeast mutants.

6. The method according to claim 1, wherein said fermentation is carried out at a temperature of greater than 21° C.

7. The method according to claim 1 or 6, wherein said fermentation is carried out under continuous or periodic gassing.

8. The method according to claim 7, wherein said gassing process is carried out once a day for 15 to 30 minutes.

9. The method according to claim 7, wherein air, inert gas or mixtures thereof are used in the gassing process.

* * * * *